(12) United States Patent
Sandfort (10) Patent No.: US 12,026,853 B2
(45) Date of Patent: Jul. 2, 2024

(54) DEEP LEARNING BASED DENOISING AND ARTIFACT REDUCTION IN CARDIAC CT CINE IMAGING

(71) Applicant: The Board of Trustees of the Leland Stanford Junior University, Stanford, CA (US)

(72) Inventor: Veit Sandfort, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 435 days.

(21) Appl. No.: 17/392,584

(22) Filed: Aug. 3, 2021

(65) Prior Publication Data

US 2022/0036517 A1    Feb. 3, 2022

Related U.S. Application Data

(60) Provisional application No. 63/060,580, filed on Aug. 3, 2020.

(51) Int. Cl.
*G06T 7/50*       (2017.01)
*G06N 3/04*       (2023.01)
(Continued)

(52) U.S. Cl.
CPC .................. *G06T 5/70* (2024.01); *G06N 3/04* (2013.01); *G06T 5/50* (2013.01); *G16H 30/20* (2018.01);
(Continued)

(58) Field of Classification Search
CPC . G06T 5/002; G06T 5/50; G06T 2207/10076; G06T 2207/10081; G06T 2207/20081; G06T 2207/20084; G06T 2207/30048; G06T 3/4046; G06T 9/002; G06T 2207/20076; G06T 7/0012; G06T 2207/10072; G06T 11/003; G06T 2207/10104; G06T 2207/10108; G06T 2207/30004; G06T 7/55; G06T 11/05; G06T 2210/41; G06T 5/00; G06N 3/04; G06N 3/045; G06N 3/02;
(Continued)

(56) References Cited

U.S. PATENT DOCUMENTS

2018/0104940 A1\*  4/2018  Sumaru ..................... G03F 7/32
2018/0144243 A1\*  5/2018  Hsieh ....................... G06F 11/30
(Continued)

OTHER PUBLICATIONS

Zhang et al. Beyond a Gaussian Denoiser: Residual Learning of Deep CNN for Image Denoising. Aug. 13, 2016. arXiv:1608.03981v1 [cs.CV].
(Continued)

*Primary Examiner* — Jose L Couso
(74) *Attorney, Agent, or Firm* — LUMEN PATENT FIRM (57) ABSTRACT

A method for cardiac computed tomography imaging acquires 4D image volumes using cardiac CT, generates synthetic low noise data from the 4D image volumes for a complete cardiac cycle by exploiting redundancies in the data, uses the generated synthetic low noise data to train a 3D U-Net with 2D+time architecture to produce denoised cardiac CT output from noisy cardiac CT input, and uses the trained 3D U-Net for deep learning based denoising of functional cardiac CT data.

1 Claim, 8 Drawing Sheets

(51) Int. Cl.
*G06T 5/50* (2006.01)
*G06T 5/70* (2024.01)
*G16H 30/20* (2018.01)

(52) U.S. Cl.
CPC .............. *G06T 2207/10076* (2013.01); *G06T 2207/10081* (2013.01); *G06T 2207/20081* (2013.01); *G06T 2207/20084* (2013.01); *G06T 2207/30048* (2013.01)

(58) Field of Classification Search
CPC ........... G06N 3/08–088; G06N 3/0445; G06N 3/0454; G06N 3/4046; G06N 7/00; G06N 20/00; G06N 11/008; G16H 30/20; G16H 30/40; G16H 50/20; G06K 7/1482; G06V 10/454; G06V 10/54; G06V 10/774; G06V 10/82; G06V 30/18057; G06V 10/30; Y10S 128/925; A61B 5/7267; A61B 6/032; A61B 2290/3762; A61B 5/0073; A61B 6/037; A61B 6/5205; A61B 6/5258; A61B 5/0033
See application file for complete search history.

(56) References Cited

U.S. PATENT DOCUMENTS

| | | | |
|---|---|---|---|
| 2018/0144465 A1* | 5/2018 | Hsieh | G16H 30/40 |
| 2018/0240219 A1* | 8/2018 | Mentl | G06T 11/008 |
| 2019/0108904 A1* | 4/2019 | Zhou | G06T 5/002 |
| 2020/0118306 A1* | 4/2020 | Ye | G06T 11/003 |
| 2021/0192810 A1* | 6/2021 | Paysan | G06T 7/0012 |
| 2021/0295474 A1* | 9/2021 | Wang | G06N 3/084 |

OTHER PUBLICATIONS

Rolnick et al. Deep Learning is Robust to Massive Label Noise. May 30, 2017. arXiv:1705.10694v3 [cs.LG].

Isensee et al. Brain Tumor Segmentation and Radiomics Survival Prediction: Contribution to the BRATS 2017 Challenge. Feb. 28, 2018. arXiv:1802.10508v1 [cs.CV].

Çiçek et al. 3D U-Net: Learning Dense Volumetric Segmentation from Sparse Annotation. Jun. 21, 2016. arXiv:1606.06650v1 [cs.CV].

Zhao H, Gallo O, Frosio I, Kautz J. Loss Functions for Image Restoration With Neural Networks. Nov. 28, 2015. arXiv:1511.08861v3 [cs.CV].

* cited by examiner

DEEP LEARNING BASED DENOISING AND ARTIFACT REDUCTION IN CARDIAC CT CINE IMAGING

CROSS-REFERENCE TO RELATED APPLICATIONS

This application claims priority from U.S. Provisional Patent Application 63/060,580 filed Aug. 3, 2020, which is incorporated herein by reference.

FIELD OF THE INVENTION

The present invention relates generally to methods for diagnostic imaging. More specifically, it relates to cardiac computed tomography (CT) imaging techniques.

BACKGROUND OF THE INVENTION

Cardiac CT has become a cornerstone of cardiac diagnostics due to its lower radiation dose techniques, higher image quality, increased evidence of diagnostic performance resulting in increased confidence of clinicians in the technology. Retrospectively gated studies are frequently performed due to their robustness and reliability. Dose modulation techniques enable electrocardiography (ECG) gated retrospective CT acquisitions with low radiation doses during most phases of the cardiac cycle, except for a predefined higher dose phase (e.g., end-diastolic phase). Functional image information has additional value compared to coronary static morphology alone, which has been shown in acute chest pain patients (1). But in dose modulated scans, due to high noise and additional artifacts in the low-dose phases, these functional images are often not usable for diagnostic purposes and pose a challenge for automatic functional analysis.

Prior research attempted to denoise the high noise portion of the data. The major issue is that no ground truth data is available for the high noise portion. In theory, one could acquire a low dose and a high dose scan of a patient but this would require additional radiation and therefore is not practical for acquisition in a large number of patients. Additionally, there are unresolved issues such as motion between scans and different contrast material concentrations. Kang et al. (2) recognized these challenges and aimed to use unpaired data by using a CycleGAN to learn denoising of the high noise portions. Another approach to overcome the lack of ground truth data is to create synthetic high noise data and use a convolutional neural network (CNN) to reconstruct the original data (3). The issue here is that—especially in the very low dose setting—it can be quite difficult to correctly simulate CT noise characteristics and this may require full physical simulation of the CT including detector characteristics.

Zhang et al. (4) performed denoising using a CNN by conditioning the network on the residual, i.e., the difference between noisy and denoised images. This means that the network learns to predict the noise pattern which is then subtracted from the noisy input image. Zhang's approach resulted in improved performance but this method did not utilize multiple cardiac phases.

SUMMARY OF THE INVENTION

The present description provides a deep learning method for denoising functional cardiac imaging taking advantage of multiphase information in a 3D (2D+time) neural network. Previous methods typically do not leverage the fact that a very similar high-quality time frame is available and, therefore, each time point should ideally not be analyzed in isolation but all available data should be used for denoising. Deep learning denoising using the present 3D (2D+time) approach results in excellent denoising performance and facilitates valid automatic processing of cardiac functional imaging.

In one aspect, the present invention provides a method to generate synthetic low noise data for the complete cycle and use this data to train a 3D Unet with time as the third dimension for deep learning based denoising. The use of synthetic low noise data is a key component, as acquiring factual training data is extremely expensive and likely not feasible at a large scale due to radiation safety concerns. The synthetic low noise data is artificially generated data from the 4D time series exploiting redundancies in the data and containing low noise images throughout the cardiac cycle.

The 2D+time architecture of the deep learning method is another key component. Intuitively, the deep learning method will benefit from having access to the low noise portions of the exam when attempting to remove noise from the high noise portion. While we used the Unet as a base architecture the 2D+t time approach can be applied to any 3D capable deep learning architecture.

To create the synthetic low noise data, extensive image registration within the 4D volume is performed. Briefly, the lowest noise time point is selected and then coregistered to all other time points using non-rigid constrained coregistration. Manual parameter tuning may be used. Although coregistration imperfections are possible, the vast majority of voxels provide a good fit and therefore this method enables training of deep learning models.

In one aspect, the invention provides a method for cardiac computed tomography imaging, the method comprising: a) acquiring 4D image volumes (i.e., time series of 3D images) using cardiac CT; b) generating synthetic low noise data from the 4D image volumes for a complete cardiac cycle by exploiting redundancies in the data; c) using the generated synthetic low noise data to train a 3D U-Net to produce denoised cardiac CT output from noisy cardiac CT input, wherein the 3D U-Net has a 2D+time architecture; and d) using the trained 3D U-Net for deep learning based denoising of functional cardiac CT data. Preferably, generating synthetic low noise data comprises performing image registration within the 4D image volume by selecting a lowest noise time point; and performing co-registration of the lowest noise time point with other time points using non-rigid constrained co-registration.

In another aspect, the invention provides a method for cardiac computed tomography imaging, the method comprising: a) acquiring 4D image volumes using cardiac CT; b) using a trained 3D U-Net to generate denoised functional cardiac CT data from the acquired 4D image volumes; wherein the 3D U-Net has a 2D+time architecture and is trained using training data to produce denoised cardiac CT output from noisy cardiac CT input, wherein the training data comprises synthetic low noise data from 4D image volumes.

DETAILED DESCRIPTION OF THE INVENTION

Embodiments of the present invention provide a deep learning based method to use a maximum of information from the high and low noise cardiac phases for denoising and artifact removal. The technique creates synthetic ground truth data using image coregistration to register the lowest noise time point with the higher noise time points. This is computationally expensive but still may be performed retrospectively in a larger number of patients. The synthetic labels are plausible in the vast majority of pixels and deep learning has been shown to tolerate imperfect labels (5). Using these synthetic data enables training of a U-net with improved denoising performance compared to conventional methods. In addition, a 3D U-net with time as the third dimension (2D+time) is superior to a 2D U-net, which has no access to prior and later time points.

This high-performance CT denoising enables automated functional imaging in a much larger fraction of patients. This also enables advanced functional analysis in the future such as strain or local deformation analysis without a significant increase in radiation dose.

Figure 7:
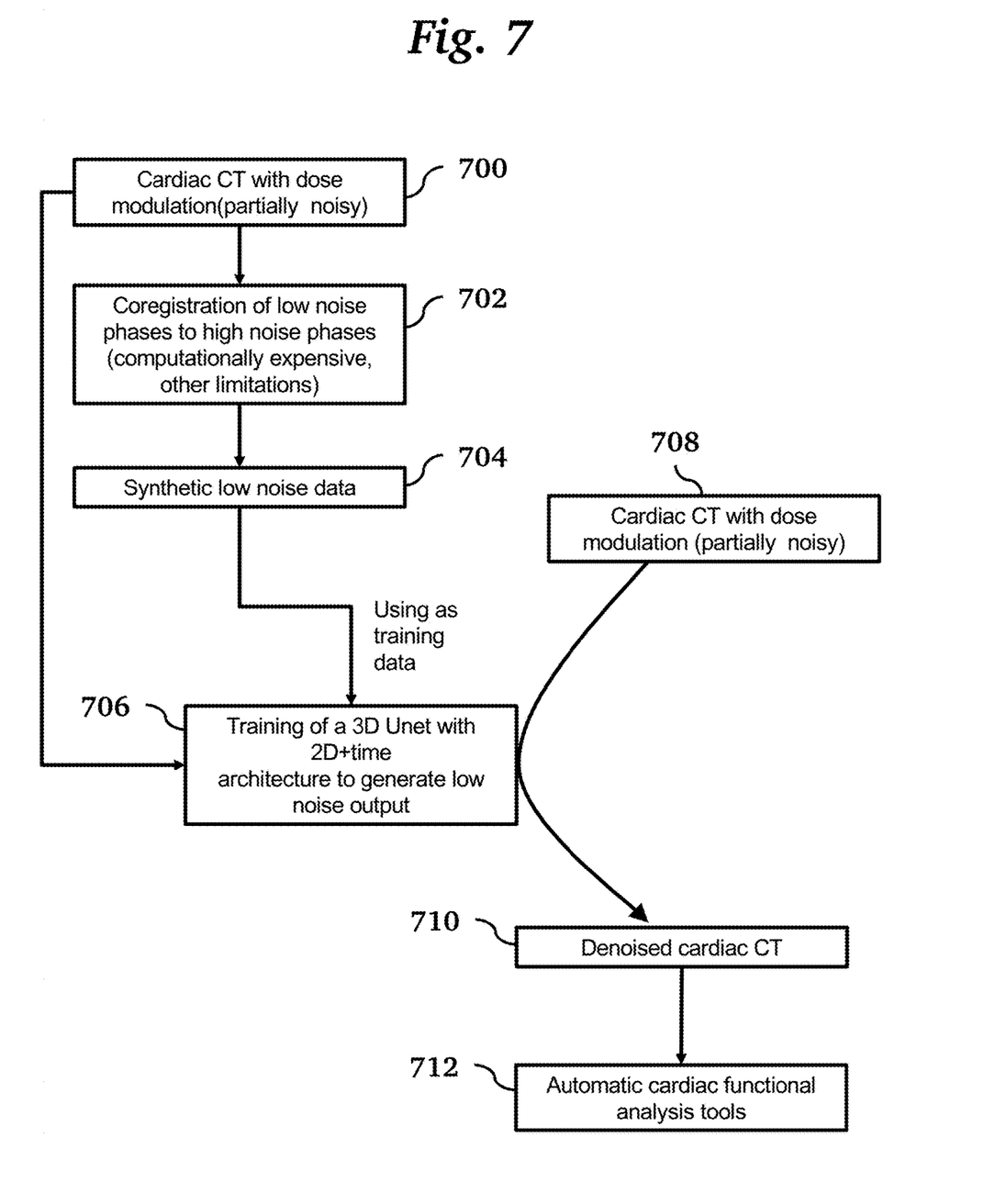
FIG. 7 provides an overview of a processing pipeline of a method according to an embodiment of the invention.

FIG. 7 provides an overview of a processing pipeline of a method according to an embodiment of the invention. In step 700, cardiac CT is performed with dose modulation. In step 702, coregistration of low noise phases to high noise phases is performed. In step 704, synthetic low noise dataset is collected and stored. In step 706, a 3D Unet is trained with 2D+time architecture to generate low noise output from cardiac CT with dose modulation. This trained 3D U-net is then used to generate denoised cardiac CT images 710 from cardiac CT data with dose modulation 708, which is partially noisy. The denoised cardiac CT images 710 may then be used for automatic cardiac functional analysis 712.

The techniques will now be illustrated in more detail by describing an example retrospective study. Data of 566 consecutive adult patients undergoing cardiac CT with dose modulated retrospective gating were acquired from the clinical picture archiving and communication system and data were anonymized at the time of download. Cardiac CT was performed on a dual-source CT scanner (Siemens Force, Forchheim, Germany) using 80-120 kVp based on scanner selection (CareKV). The reconstruction kernel was Bf32 and slice thickness was 2 mm, slice separation was 2 mm with reduced reconstruction matrix size ('functional matrix', 256×256). Data were fully anonymized at the time of download. Functional cardiac CT resulted in 4D datasets with 256×256 images, 40-90 slices, and 20 time points. For computational purposes, we reduced the dimension of the image data to 128×128 pixels by scaling and to 10 timepoints by omission of every second timepoint while the number of z-slices was left unchanged. This also brings the data into a more isotropic format. For our 2D+t U-net architecture we preprocessed data selecting a single slice and 10 timepoints as a 3D dataset with padding of 3 slices (in a 'wrap-around' fashion, so that the last 3 frames of the cycle are padded at the beginning and vice-versa) along the time axis resulting in the final dimensions of 128×128×16. This was done to provide enough context for the deep learning methods for the time points at the beginning and end of the cardiac cycle. As each patient scan contained a different number of slices, the final dataset consisted of 29,699, 3,087, and 3,325 time series for training, validation, and test data sets, respectively. In line with basic machine learning procedures care was taken to ensure that data of each patient were exclusively in either the training, validation or test data set.

Generation of Synthetic Denoised Data

Dose modulated cardiac image sequences contain multiple time points with varying levels of noise and artifacts. We selected the time point with the lowest noise level and used non-rigid image coregistration to deform this frame to match each of the other, higher noise frames, thereby generating a low noise synthetic time series. While this synthetic data is imperfect, it will be reasonably correct for the large majority of pixels and therefore will enable a deep learning method to learn the CT noise characteristics and to successfully denoise images. For non-rigid image coregistration we used the freely available software elastix (6). A spline transformation was performed and we used the mutual information metric for optimization. In addition, to avoid extreme deformations occurring when registering to noisy images, we used a bending energy penalty term (7). Noise processing was performed to facilitate coregistration but of note, this was not applied to the final transformed images. Image coregistration took approximately 2 hours for each scan (4 CPU cores).

Deep Learning U-Net

The U-net architecture was developed for segmentation tasks but has been shown to be efficient for denoising and image restoration tasks as well. We used a modified U-net with residual connections and group normalization (8-11). Kernel size was 3. We decided to use a $l_1$ loss function because preliminary image assessment was more promising and it has been previously shown that $l_1$ loss leads to less artifacts and subjectively cleaner images compared to $l_2$ loss (12). We used 64 initial feature maps, the learning rate was 0.0001 and the Adam optimizer was used. Batch size was 4. Basic data augmentation with flips and rotations was performed. Input data were normalized to a mean of 0 and a standard deviation of 1. The observed validation loss continued to improve for approximately 120 k iterations, therefore all experiments were performed with 120 k iterations, corresponding to approximately 13 epochs (see supplementary data for an example learning curve). The model yielding the lowest validation loss was used for further testing.

Figure 8:
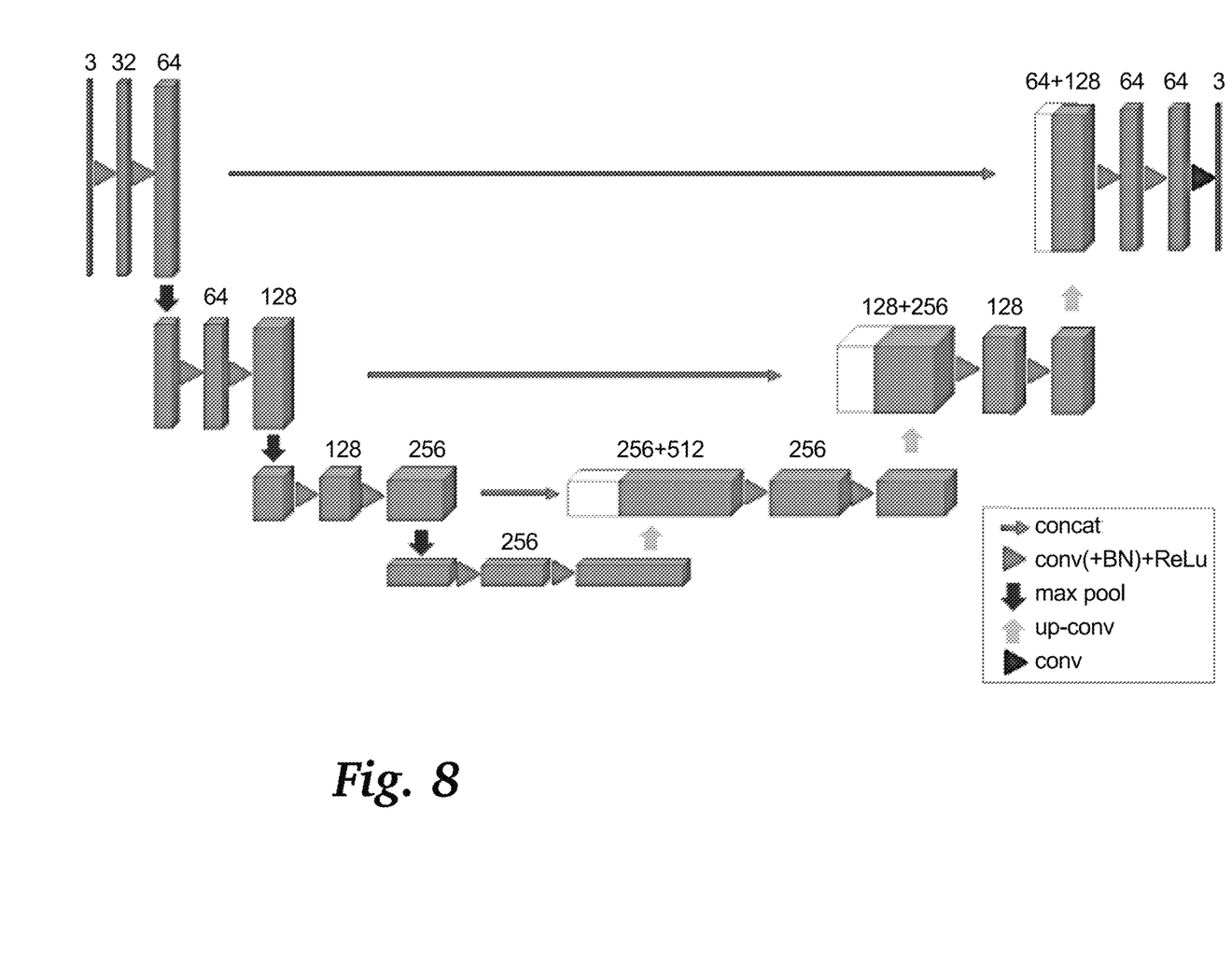
FIG. 8 provides an overview of a 3D (2D+time) neural network architecture according to an embodiment of the invention.

When looking at an image in a time series it is beneficial to look at prior and consecutive frames to gather additional context. To exploit this data relationship, we used a 3D U-net with 2 spatial dimensions and one temporal dimension (2d+t), as shown in FIG. 8. For comparison, we also trained a U-net with pure 2D convolutions without a temporal component.

Training was performed on HPC nodes (Nero cluster) using 2 NVIDIA V100 GPUs. GPU memory utilization was approximately 9 GB per GPU and training took approximately 14 hours.

Comparison Denoising Standard Algorithm

For comparison we used the standard denoising algorithm BM3D (pybm3d implementation) which has been shown to reliably deliver good results over a vast range of applications.

Evaluation

Objective Measurements

For image quality evaluation we used a commonly used method with noise defined as the standard deviation of CT numbers of a ROI placed in the blood pool in the left ventricle with the assumption that the blood pool has a uniform attenuation and noise can reliably be quantified using standard deviation (standard practice). We also calculated signal to noise ratio (SNR) by the formula mean/standard deviation of CT numbers within the blood pool ROI. The rationale is that for LV segmentation the main signal is the LV blood pool contrast enhancement which may be impaired by a certain level of noise in the blood pool. These measurements and calculations were performed for each frame in a time series.

Observer Evaluation

Experienced physician readers (>5 years of cardiovascular imaging experience) evaluated the overall image quality, the noise level and the amount of artifacts present using predefined criteria on a scale from 1-5 (with 5 describing the highest image quality). Raters had access to the full time series and were instructed to score the most problematic frame of each time series. Images were presented blinded and in random order (N=50 patients). Example images for each quality grade were provided to instruct reviewers for standardized rating.

Evaluation of LV Segmentation Performance

To evaluate the utility of denoised CT images for LV segmentation we used processed images as input for a simple threshold-based LV segmentation algorithm and compared results to an expert manual segmentation (20 patients, single slice, 10 frames, resulting in 200 segmentations). We used 3D Unet denoised images and BM3D denoised images as inputs. In a preprocessing step, all high attenuation areas which are not within the LV (e.g. bones or the left atrium) were manually masked. A threshold for LV segmentation was selected based on mean LV blood pool attenuation multiplied by 0.75. All unmasked pixels above the threshold were considered to be LV lumen.

We then compared LV area measurement results by slice with the ground truth of the expert segmentation (physician >5 years of cardiac imaging experience) performed on the unprocessed images using intraclass correlation coefficient and Bland-Altman analysis.

In addition to this per-frame analysis we performed analyses of the LV area ejection fraction. The area ejection fraction of a slice timeseries was calculated as follows:

$$LVEFArea=(1-minimumArea/maximumArea)*100.$$

Statistics

R version 4.0 was used for all analyses. For comparison of multiple measurements on a set of patient images the Friedman test with a post-hoc paired Conover test with Bonferroni adjustment was performed (R package PCMCR). For LV area and LVEF measurement comparisons intraclass correlation coefficients with confidence intervals were calculated (R package psych, ICC3, fixed raters). Significance testing was performed using bootstrapping (n=1000). In addition, Bland-Altman analysis was performed (R package blandr). Significance at the level of p<0.05 was assumed when confidence intervals were not overlapping.

Results

Figure 1:
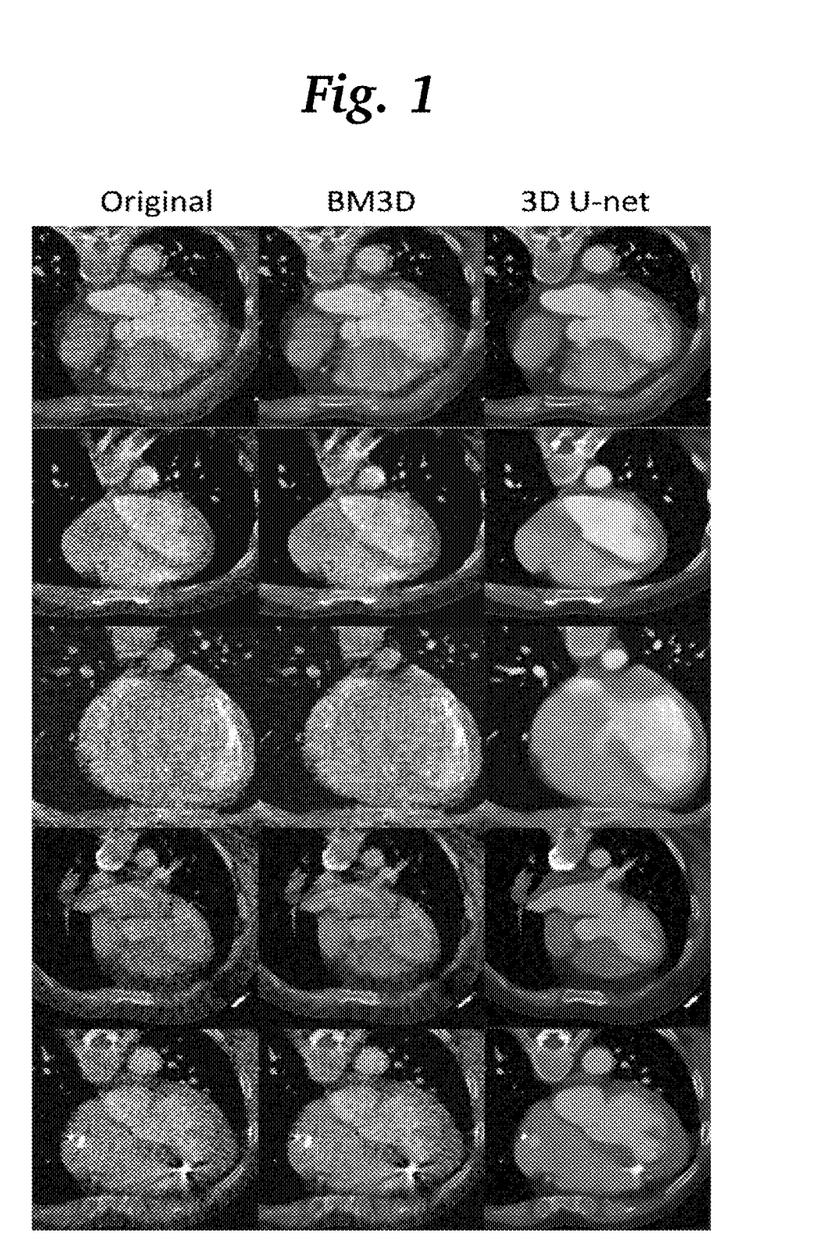
FIG. 1 is a collection of example images of various noise and artifact levels for unprocessed images (left column), BM3D (which is an industry standard denoising method) processed images (middle column) and 3D U-net processed images (right column).

FIG. 1 shows several example images of various noise levels. The images show plausible left ventricular contours and robustness to a wide range of noise levels for the 3D U-net denoising method.

Noise Measurements

Cardiac Cycle Analysis

Figure 2:
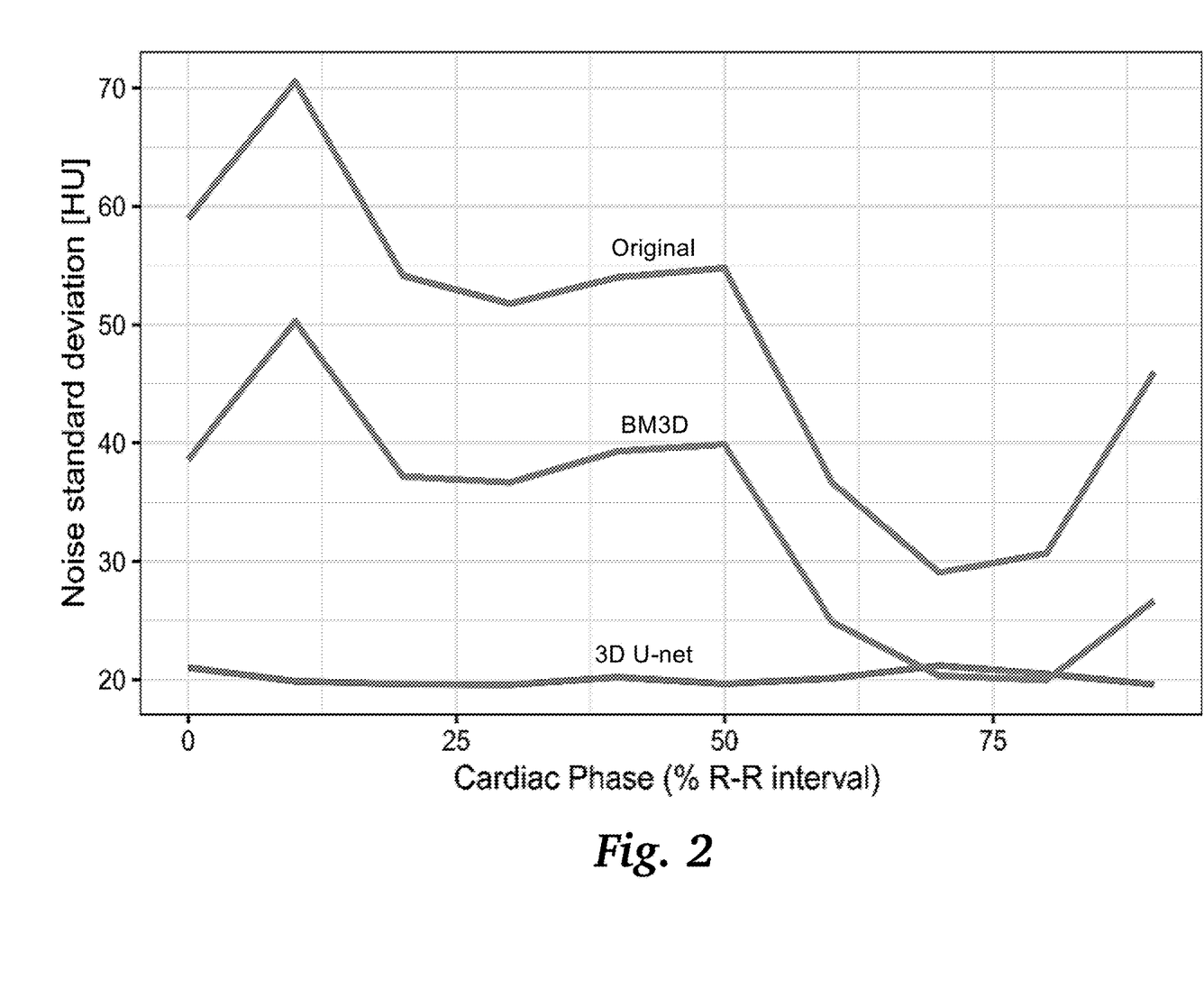
FIG. 2 is a graph of noise levels (standard deviation of blood pool) over the cardiac cycle (% RR interval). 3D U-net shows consistently low noise characteristics over the cardiac cycle.

Noise was measured as standard deviation of blood pool Hounsfield units. The noise levels vary considerably over the cardiac cycle as can be seen in FIG. 2. At around 70-80% of the cardiac cycle, the lowest noise levels are achieved which is the intent of the dose modulation technique. Ideally, for the functional analysis, low noise images would be available throughout the cardiac cycle and the highest noise and most problematic time point impacts the analysis the most. It is clear from FIG. 2 that the 3D U-net achieves significantly lower noise especially in the lower dose sections of the cardiac cycle.

Mean and Highest Noise Measurements

Figure 3:
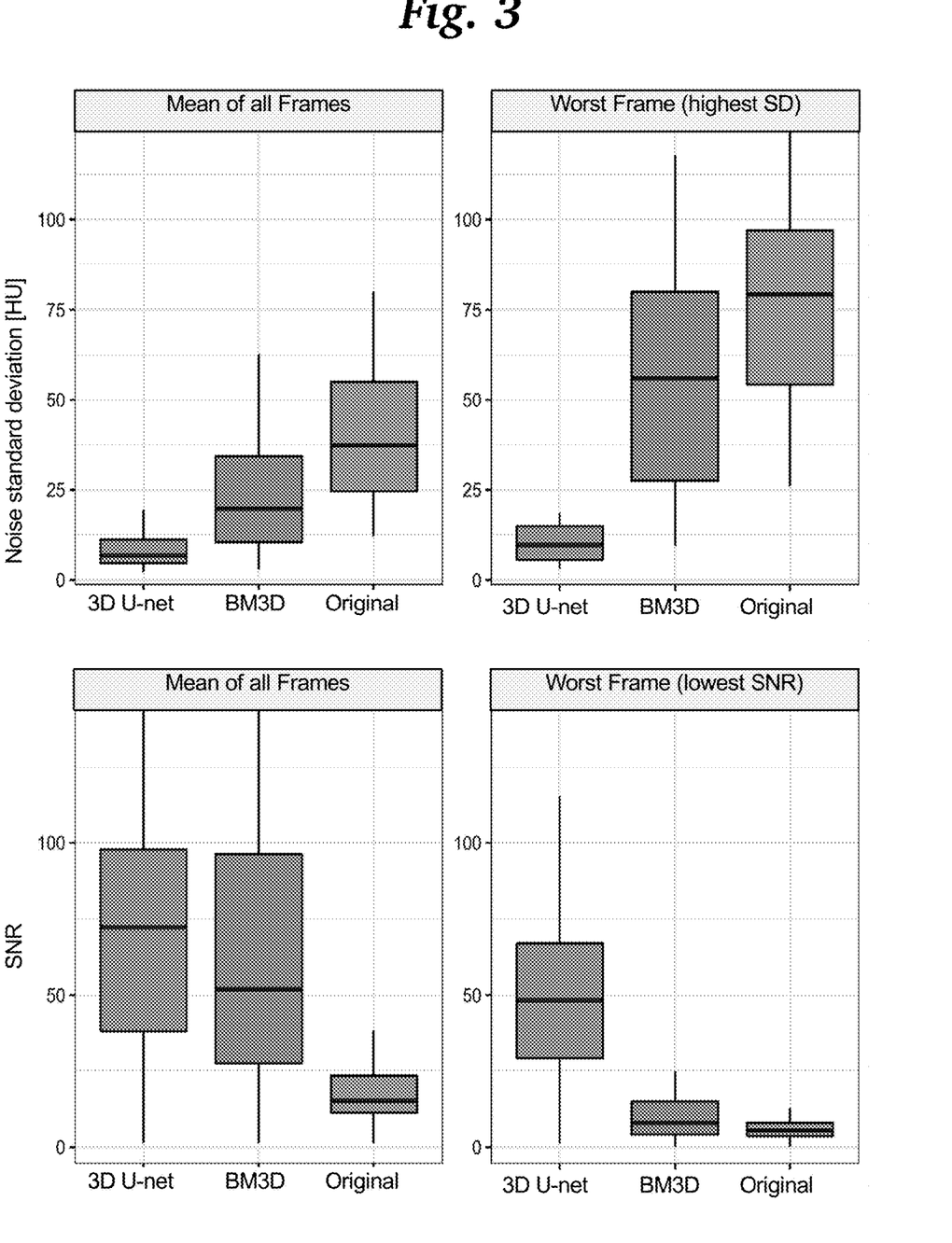
FIG. 3 illustrate results for noise measurements which are shown using standard deviation of noise (upper panel) and signal to noise ratio (SNR, lower panel) measured within the LV cavity. The left side shows mean measurements including all time frames of the cardiac cycle while the right side shows the results for the most problematic time frame which usually limits quantitative functional analysis.

Despite the variance of noise over time, we performed an analysis of the average blood pool noise level (standard deviation). FIG. 3 and Table 1 show that 3D U-net denoising provides superior results compared to BM3D t (p<0.0001).

TABLE 1

| Analysis Type | Noise SD | | | Analysis Type | SNR | | |
|---|---|---|---|---|---|---|---|
| | Method | Mean | SD | | Method | Mean | SD |
| Highest | 3D U-net | 23.97 | 44.07 | Lowest | 3D U-net | 47.12 | 28.74 |
| | 2D U-net | 57.74 | 42.90 | | 2D U-net | 10.08 | 9.17 |
| | BM3D | 60.86 | 43.95 | | BM3D | 11.27 | 10.15 |
| | Original | 79.75 | 39.39 | | Original | 6.48 | 4.72 |
| Mean | 3D U-net | 20.32 | 42.52 | Mean | 3D U-net | 67.64 | 41.47 |
| | 2D U-net | 35.22 | 39.22 | | 2D U-net | 29.95 | 19.35 |
| | BM3D | 33.37 | 39.84 | | BM3D | 62.03 | 43.92 |
| | Original | 48.66 | 37.13 | | Original | 17.36 | 9.27 |

In clinical practice, the limiting factor for advanced functional analysis is the lowest dose and highest noise time point of the cardiac cycle. Therefore, we also performed an analysis based on the highest noise occurrence in each time series. Results shown in FIG. 3 indicate that the advantage of the 3D U-net is more pronounced for the most critical time points compared to the average values (24.0 HU vs. 60.8 HU for 3D U-net and BM3D, respectively, $p<0.0001$).

Signal to Noise Ratio

Signal to noise ratio (SNR) was calculated for the blood pool and results are shown in FIG. 3 and Table 1. In line with findings of noise levels, the deep learning based denoising method showed superior results on analysis of mean and lowest SNR per time series ($p<0.0001$).

Observer Evaluation

Figure 4:
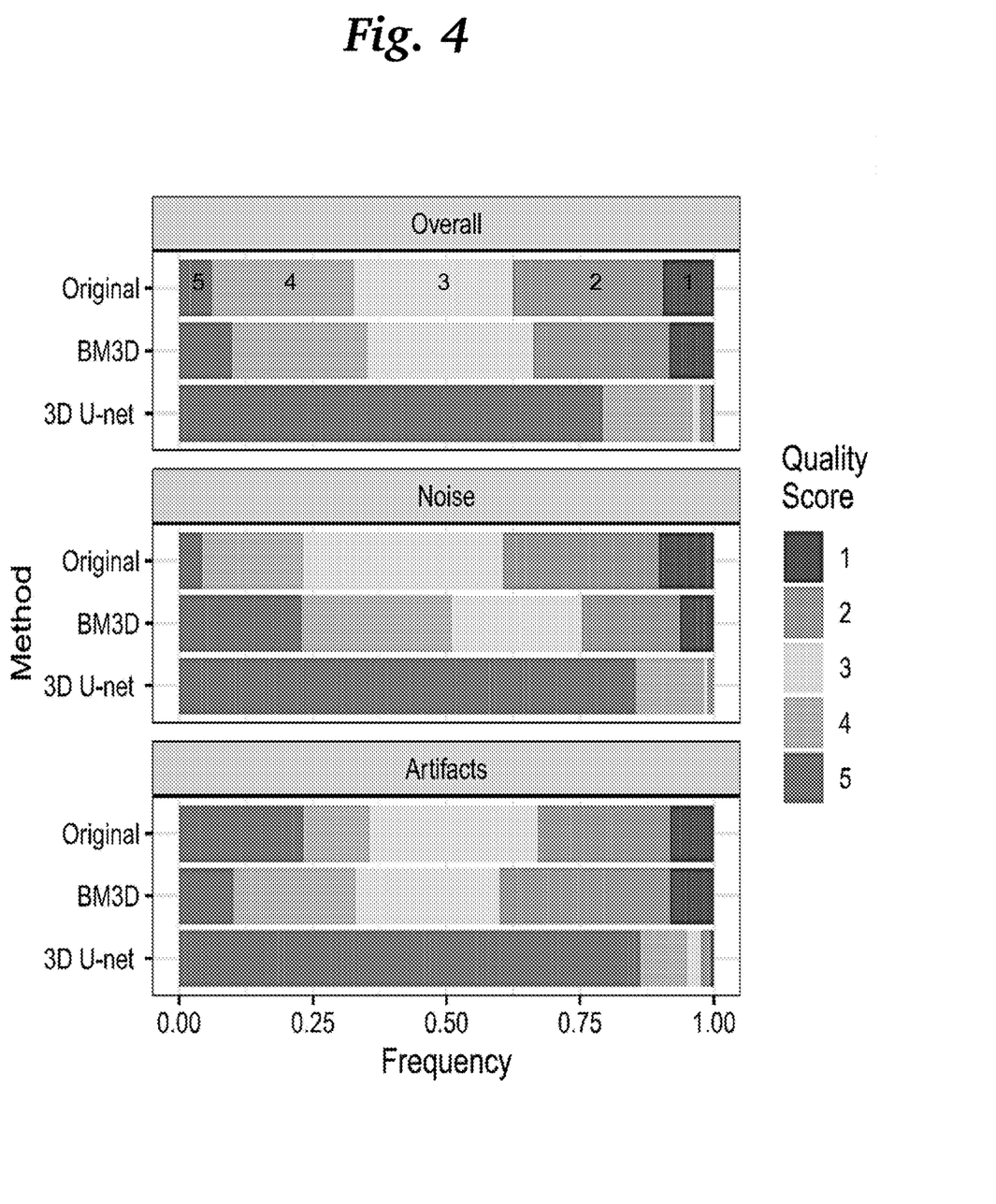
FIG. 4 shows expert evaluations of overall image quality (upper panel), noise related image quality (middle panel) and artifact related image quality (lower panel) using a quality score from 1 (red, unusable) to 5 (dark green, excellent quality). The 3D U-net clearly has the highest proportion of very high quality scores in all 3 categories by a large margin (dark green bar). The BM3D images show higher quality scores in the noise category compared to the unprocessed images (middle panel). Of note, the quality scores in regard to artifacts are lower for BM3D images compared to unprocessed images (lower panel).

FIG. 4 demonstrates that the 3D U-net achieved meaningfully higher image quality in all subcategories (overall quality, noise, and artifacts, $p<0.0001$ for all evaluated image characteristics). The median overall image quality score was 5 (IQR 4-5) for the 3D U-net compared to 2 (IQR 2-3) for BM3D and 2 (IQR 2-3) for the original images. (Excellent quality described by a score of 5 and nondiagnostic quality by a score of 1).

Evaluation of LV Segmentation Performance

LV Area Measurements

Figure 5:
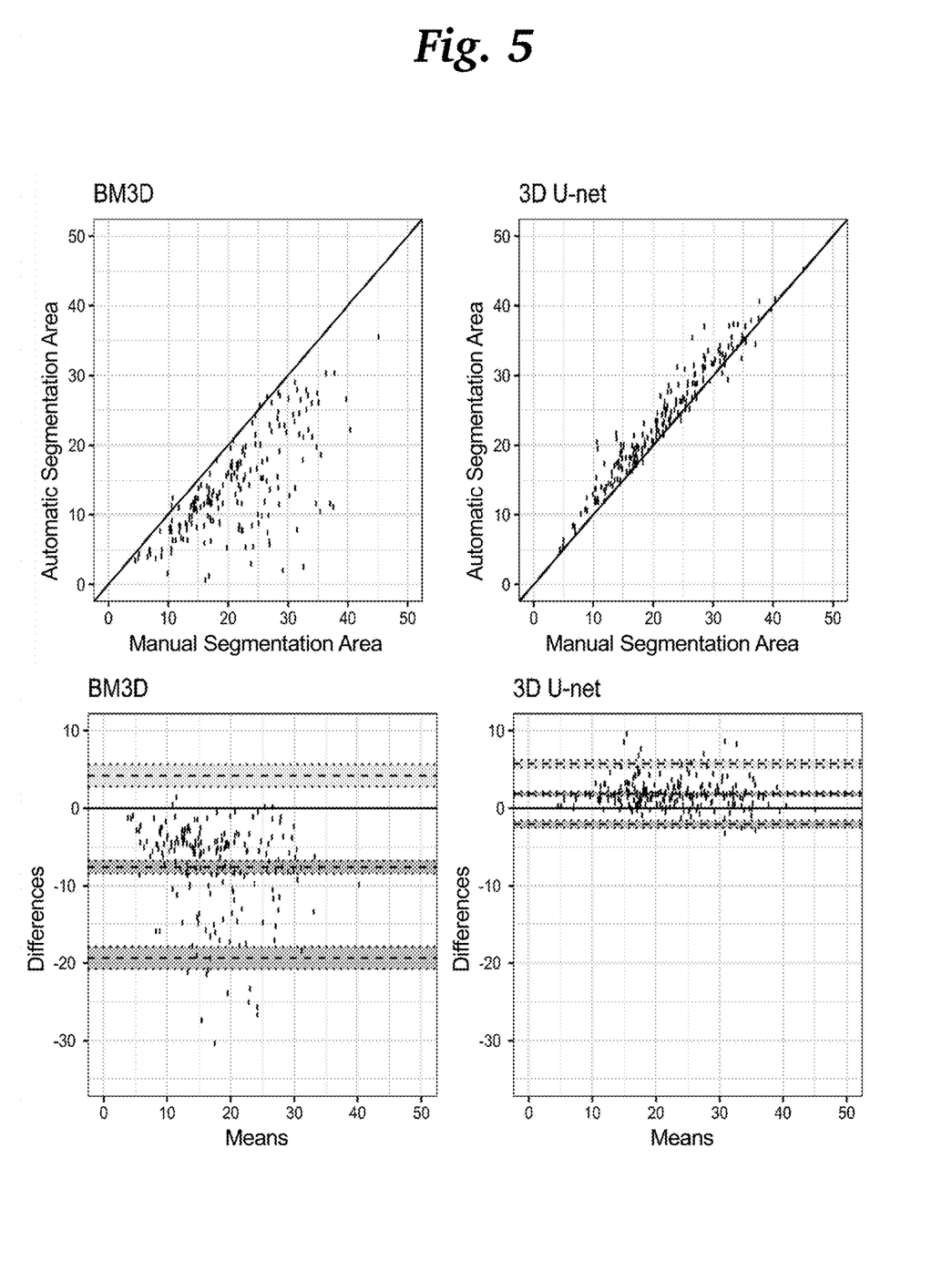
FIG. 5 shows graphs comparing the 3D U-net with BM3D. Denoised images were used as inputs for a threshold based LV segmentation algorithm and LV area measurement (units: cm$^2$) were compared to manual segmentation results. The left panel shows results for BM3D denoised images and shows poor agreement. The right panel shows data for the LV area measurements based on 3D Unet denoised images which demonstrates excellent agreement with manual measurements.
Figure 6:
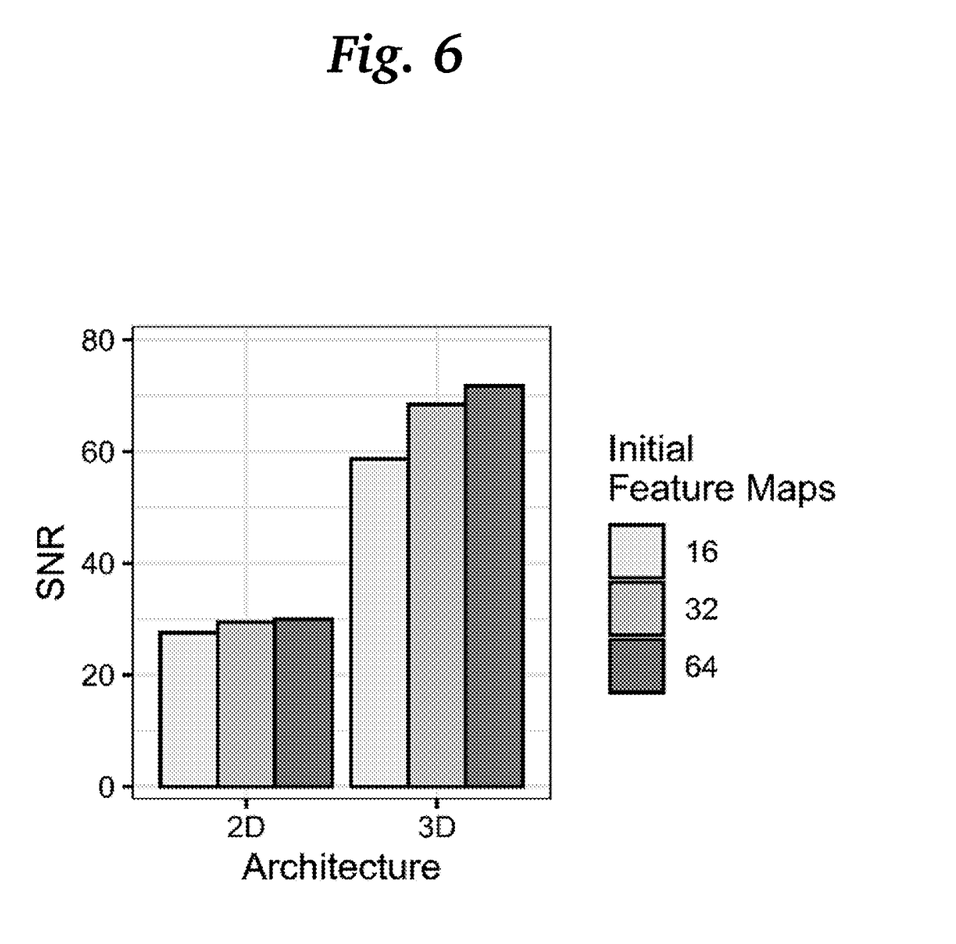
FIG. 6 shows a graph of signal to noise ratio (SNR) for different neural network architectures (2D versus 3D U-net and number of feature maps 16/32/64) in a post-hoc analysis. The 3D U-nets show clearly higher SNR values compared to 2D U-nets (3D SNR 71.8±47.2 vs. 2D SNR 29.9±27.6 for 64 feature maps). In addition, especially with the 3D architecture the network benefits from more feature maps with 64 initial feature maps giving the best results.

Using a threshold-based segmentation algorithm and using the 3D Unet denoised images as input, the agreement of automatic LV area measurements with the reference standard of manual expert segmentation was excellent (ICC 0.97, CI 0.96-0.98, see FIG. 5). When using BM3D denoised images as input for the segmentation algorithm agreement with the reference standard was moderate (ICC 0.69, CI 0.61-0.75, see FIG. 5). The difference between these ICC values was statistically significant ($p<0.001$).

In addition, we performed a Bland-Altman analysis (FIG. 5) which showed significantly more bias for the BM3D based measurements compared to 3D Unet based measurements (bias of −7.6 cm2 [CI −6.75 to −8.43] and 1.83 cm2 [CI 1.56 to 2.11], respectively). Bland-Altman plotting also shows that the limits of agreement are significantly narrower for the 3D Unet image-based measurements.

LV Area Ejection Fraction Measurements

A slice-based area ejection fraction was calculated using a threshold-based mechanism using BM3D and deep learning denoised images as input. Bland-Altman analysis showed that deep learning denoised images enabled improved LVEFArea measurements with significantly narrower limits of agreement for deep learning based images (limits of agreement −18.14 to 7.20 for deep-learning-based images vs. −16.56 to 45.11 for BM3D based images, $p<0.05$).

Secondary Analysis of Performance of Various Network Architectures

To evaluate the significance of using a 3D U-net compared to simpler network architectures we performed additional analysis with a 2D U-net. In addition, we tested lower complexity networks by reducing the number of initial feature maps from 64 to 32 and 16. FIG. 5 indicates that the 3D (2D+t) architecture has a strong advantage compared to 2D U-net, for example, the 64 feature 3D U-net showed an SNR of 71.8±47.2 compared to SNR 29.9±27.6 for the 2D U-net ($p<0.0001$).

For the 3D U-net, increasing the complexity per number of initial feature maps increases performance. Based on these findings the optimal performance is achieved with a 3D U-net with at least 64 initial feature maps.

DISCUSSION

We hypothesized that synthetic low noise CT data generated by deformation of cine images can be used to train a deep learning network to denoise functional CT images. In addition, we hypothesized that a 3D network with time as the third dimension (2D+t) would lead to higher performance compared to a 2D architecture.

Our results show that a 3D U-net trained with the synthetic data is highly effective in removing noise from the high noise portions of the cardiac cycle. Noise quantified by standard deviation of blood pool pixels was significantly decreased. The 3D U-net outperformed sophisticated conventional denoising methods like BM3D by a clinically meaningful margin with a subjectively obvious improvement.

The performance metrics of the 2D U-net approach were more in line with conventional methods and this network was significantly less effective compared to a 3D U-net. This finding indicates that receiving the full information of the cardiac cycle including low and high noise portions is the key to allow the neural network to successfully remove severe noise and noise-related artifacts from the time series. A large body of literature exists on the issue of denoising of static CT images using a variety of algorithms (13) but the specific application of cardiac CT with a multi-timepoint acquisition poses specific challenges and opportunities for image processing which are not present in routine CT and are rarely addressed in research.

The expert assessment of image quality corroborated these objective measures with significantly higher image quality scores for the 3D U-net processed images as compared to BM3D. Of note, the majority (>75%) of the 3D U-net processed images was considered to be of excellent image quality.

These results show that deep learning based denoising results in higher image quality with lower noise and higher expert ratings for image quality. The question remains if measurements performed on denoised images are indeed valid. Therefore, we performed a comparison of LV measurements from a threshold-based automatic segmentation algorithm using preprocessed images as input with LV measurements from manual expert segmentations. Using the deep learning denoised images as inputs for the segmentation resulted in excellent agreement with expert measurements. This shows that while deep learning based denoising is currently a 'black box' process, the denoised images may be very well suited for LV quantitative evaluation and result in valid measurements. Of note, using BM3D denoised images for segmentation resulted in significantly poorer performance which shows that the technical advantages of the deep learning method can translate into meaningfully improved performance in common clinical imaging tasks. This was reiterated in area based LVEF measurements, which were more reliable using deep learning processed images compared to BM3D.

Based on these observations it is reasonable to assume that automatic functional analysis will be possible in a larger proportion of patients receiving dose modulated CT scans and may become a routine item of cardiac CT. In addition, the improved image quality may enable routine regional functional analysis in low dose cardiac CT in the future.

While our data set is relatively large, it originates from a single center which limits the variability of the scans. Based on the method we used to generate training data it is perceivable that small, fast-moving structures like valves may not be well delineated. The focus of the current work, however, is specifically on cardiac functional analysis where these effects do not play a relevant role. All images in the example discussed were reconstructed using the same kernel and were acquired with a CT scanners from a single vendor, due to the reduced resolution used in this study, the effects of different reconstruction kernels are not expected to be an issue.

We used a simple 2D thresholding technology for automated analysis of the LV as a proof of concept. Analysis of LV volumes over time using more sophisticated computer vision methods (including commercially available tools and deep learning) are also envisioned.

Of note, the present method of generation of synthetic data can be combined with other methods to generate synthetic data such as using low noise data of a complete cardiac cycle and simulation of additional CT noise (which has other limitations such as limited data availability, biased patient spectrum and uncertainty on correct noise simulation).

CT scanners may use this method to produce improved output for cardiac functional analysis. CT cardiac analysis software would also greatly benefit from this method by improving the tools and user experience of cardiac functional analysis. Specifically, to calculate cardiac chamber sizes and ejection fraction ideally the chambers are segmented over the complete cardiac cycle. This often fails, especially in high noise portions of the exam in practice when using common commercial software packages and extensive user interaction is required for manual correction. Therefore, complete cardiac quantification is underutilized in CT cardiac imaging.

REFERENCES

1. Schlett C L, Banerji D, Siegel E, et al. Prognostic value of CT angiography for major adverse cardiac events in patients with acute chest pain from the emergency department: 2-year outcomes of the ROMICAT trial. JACC Cardiovasc Imaging. 2011; 4(5):481-491.
2. Kang E, Koo H J, Yang D H, Seo J B, Ye J C. Cycle-consistent adversarial denoising network for multiphase coronary CT angiography. Medical Physics. 2019. p. 550-562http://dx.doi.org/10.1002/mp.13284.
3. Green M, Marom E M, Konen E, Kiryati N, Mayer A. 3-D Neural denoising for low-dose Coronary CT Angiography (CCTA). Comput Med Imaging Graph. 2018; 70:185-191.
4. Zhang K, Zuo W, Chen Y, Meng D, Zhang L. Beyond a Gaussian Denoiser: Residual Learning of Deep CNN for Image Denoising. IEEE Trans Image Process. 2017; 26(7):3142-3155.
5. Rolnick D, Veit A, Belongie S, Shavit N. Deep Learning is Robust to Massive Label Noise. 2017.http://arxiv.org/abs/1705.10694. Accessed May 29, 2020.
6. Klein S, Staring M, Murphy K, Viergever M A, Pluim J P W. elastix: a toolbox for intensity-based medical image registration. IEEE Trans Med Imaging. 2010; 29(1):196-205.
7. Rueckert D, Sonoda L I, Hayes C, Hill D L, Leach M O, Hawkes D J. Nonrigid registration using free-form deformations: application to breast MR images. IEEE Trans Med Imaging. 1999; 18(8):712-721.
8. Sandfort V, Yan K, Pickhardt P J, Summers R M. Data augmentation using generative adversarial networks (CycleGAN) to improve generalizability in CT segmentation tasks. Sci Rep. 2019; 9(1):16884.
9. Isensee F, Kickingereder P, Wick W, Bendszus M, Maier-Hein K H. Brain Tumor Segmentation and Radiomics Survival Prediction: Contribution to the BRATS 2017 Challenge. Brainlesion: Glioma, Multiple Sclerosis, Stroke and Traumatic Brain Injuries. 2018. p. 287-297http://dx.dotorg/10.1007/978-3-319-75238-9_25.
10. Çiçek Ö, Abdulkadir A, Lienkamp S S, Brox T, Ronneberger O. 3D U-Net: Learning Dense Volumetric Segmentation from Sparse Annotation. Medical Image Computing and Computer-Assisted Intervention—MICCAI 2016. 2016. p. 424-432http://dx.doi.org/10.1007/978-3-319-46723-8_49.
11. Wu Y, He K. Group Normalization. Computer Vision—ECCV 2018. Springer, Cham; 2018. p. 3-19.
12. Zhao H, Gallo O, Frosio I, Kautz J. Loss Functions for Image Restoration With Neural Networks. IEEE Transactions on Computational Imaging. 2017. p. 47-57http://dx.doi.org/10.1109/tci.2016.2644865.
13. McCollough C H, Bartley A C, Carter R E, et al. Low-dose CT for the detection and classification of metastatic liver lesions: Results of the 2016 Low Dose CT Grand Challenge. Med Phys. 2017; 44(10):e339-e352.

The invention claimed is:
1. A method for cardiac computed tomography imaging, the method comprising:
   a) acquiring 4D image volumes using cardiac CT;
   b) generating synthetic low noise data from the 4D image volumes for a complete cardiac cycle by exploiting redundancies in the data;
   c) using the generated synthetic low noise data to train a 3D U-Net to produce denoised cardiac CT output from noisy cardiac CT input, wherein the 3D U-Net has a 2D+time architecture;
   d) using the trained 3D U-Net for deep learning based denoising of functional cardiac CT data;
   wherein generating synthetic low noise data comprises performing image registration within the 4D image volume by i) selecting a lowest noise time point;
ii) performing co-registration of the lowest noise time point with other time points using non-rigid constrained co-registration.

* * * * *